(12) United States Patent
Errico

(10) Patent No.: US 6,482,207 B1
(45) Date of Patent: Nov. 19, 2002

(54) EFFICIENT ASSEMBLING MODULAR LOCKING PEDICLE SCREW

(75) Inventor: Thomas J. Errico, Summit, NJ (US)

(73) Assignee: Fastenetix, LLC, Summit, NJ (US)

( * ) Notice: Subject to any disclaimer, the term of this patent is extended or adjusted under 35 U.S.C. 154(b) by 238 days.

(21) Appl. No.: 09/615,381

(22) Filed: Jul. 13, 2000

(51) Int. Cl.[7] .......................... A61B 17/70; A61B 17/56
(52) U.S. Cl. .............................. 606/61; 606/72; 606/73
(58) Field of Search ............................ 606/61, 60, 72, 606/69, 71, 70, 73

(56) References Cited

U.S. PATENT DOCUMENTS

| | | | | |
|---|---|---|---|---|
| 5,672,176 A | * | 9/1997 | Biedermann et al. | 606/61 |
| 5,735,851 A | * | 4/1998 | Errico et al. | 606/61 |
| 5,989,254 A | * | 11/1999 | Katz | 606/73 |
| 5,997,539 A | * | 12/1999 | Errico et al. | 606/61 |
| 6,077,262 A | * | 6/2000 | Schlapfer et al. | 606/61 |

* cited by examiner

Primary Examiner—John J. Wilson
Assistant Examiner—Robyn Kieu Doan
(74) Attorney, Agent, or Firm—Joseph P. Errico, Esq.; Timothy J. Bortree, Esq.

(57) ABSTRACT

A modular pedicle screw and rod implant assembly includes a shant screw, a rod holding element, a locking member, a rod, and a nut. The shant screw has a lower threaded shaft portion for insertion into the pedicle and a top shaft portion which is unthreaded, a portion of which is tapered. The locking member has a threaded upper portion and a smoothly tapered lower portion. It further includes an axial bore which is similarly tapered at the bottom for seating on the upper portion of the shant screw. This tapered bottom portion is slotted so that it may be expanded or compressed in accordance with a radial force applied thereto. The rod holding element includes two through holes; one for receiving the rod, and the other, transverse to the rod receiving hole, which is tapered. The two holes are overlapping so that when the rod is seated in the first hole and the tapered portion of the locking member is in the second hole the surfaces of the rod and the locking member are in contact. The upper portion of the locking member is threaded, and receives the nut. Tightening of the nut causes the rod and locking member to compress against one another, and for the locking member to compress against the top of the shaft screw, thus locking the assembly together securely.

12 Claims, 2 Drawing Sheets

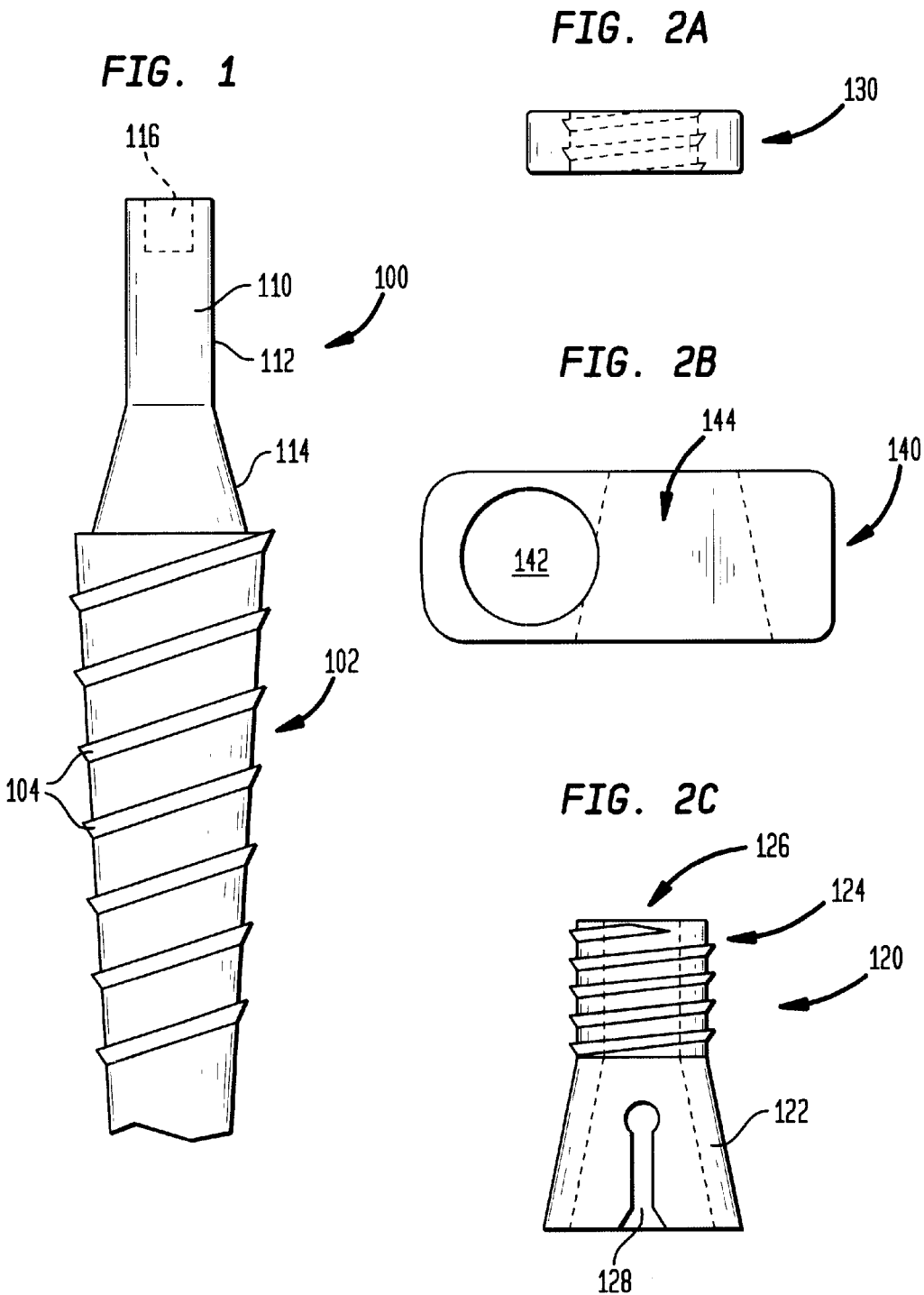

EFFICIENT ASSEMBLING MODULAR LOCKING PEDICLE SCREW

BACKGROUND OF THE INVENTION

1. Field of the Invention

This invention relates generally to a pedicle screw for use with orthopedic fixation systems having modular components, and more particularly to a pedicle screw for use in spine correction and stabilization surgery which includes an easily assembled shant screw, rod holding member, a nut, and a shant gripping and rod securing element.

2. Description of the Prior Art

The bones and connective tissue of an adult human spinal column consists of more than twenty discrete bones coupled sequentially to one another by a tri-joint complex. The anterior portion of each discrete bone is a cylindrical and disk-shaped and couples to the similar bones above and below it by means of a cartilage cushion referred to as the intervertebral disc. The posterior of each of the spinal bones comprises a shell of bone called the lamina. The lamina includes a rearwardly and downwardly extending portion called the spinous process, and laterally extending structures which are referred to as the transverse processes. The tri-joint complex then consists of the anterior intervertebral disc and two posterior facet joints which couple sequential bones via the transverse processes. The spinal cord is housed in a central canal which is disposed between the anterior vertebral body and the lamina shell.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion and/or threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. These screws are typically provided with upper portions which comprise coupling means, for receiving and securing an elongate rod therethrough. The rod extends along the axis of the spine, coupling to the plurality of screws via their coupling means. The rigidity of the rod may be utilized to align the spine in conformance with a more healthful shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsuccessful.

The art contains a variety of attempts at providing instrumentation which permit enhanced freedom for the surgeon with respect to aligning the screw and the rod, however, most are complex, inadequately reliable, and lack long-term durability. In particular, these various assemblies of the prior art fall into different classifications. The first is a simple fixed screw which receives a rod in the upper exposed portion. The rod is secured in the upper portion of the screw with either a set screw or a nut. This type of pedicle screw fixation system requires that the rod be contoured to seat in a sequence of screw heads which are often severely misaligned. A second type of pedicle screw design includes a polyaxial head on the upper portion of the screw. This polyaxial nature permits the surgeon some reprieve from having to contour the rod, however, the additional benefit is often lost in reduced locking strength of the overall device. Even with this limited flexibility, the rod often requires significant contouring. A third type of pedicle fixation system includes a series of shant screws which are coupled sequentially by a series of individual plates. While this design does eliminate the need for a contoured rod, the plates themselves occasionally require shaping. This process is more difficult, and may require multiple different shapings as each plate is separately coupled to the rods. A fourth design which has recently been introduced to the market includes a shant screw which receives a rod holding element onto the upper shaft. The rod holding element is locked onto the shant's upper shaft by a set crew. The rod is separately locked to the rod holding element by means of a side tightening nut. The design is superior to others in that it permits the surgeon to avoid any rod contouring as the rod holding elements are preloaded onto the rod and therefore need only be properly mated to the appropriate shant screws. This assembly process is cumbersome, however, inasmuch as the tightening of two separate nuts, one of which is at an odd angle to the surgeon's view, is awkward. In addition, the surgeon may not properly seat the rod holding element onto the shant screw, thus rendering the assembly prone to failure.

It is, therefore, the principal object of the present invention to provide a pedicle screw and coupling element assembly which provides the surgeon the freedom to not have to contour the rod while still having an easier and more reliable implant product.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is an easily assembled modular pedicle screw assembly for use with rod stabilization and immobilization systems in the spine. More particularly, the pedicle screw assembly of the present invention comprises: a shant screw, having a lower threaded shaft portion for insertion into the pedicle and a top shaft portion which is unthreaded; a rod holding element which includes two through holes formed therein, one for receiving the rod and the other, transverse to the rod receiving hole, which slides onto the upper shaft portion of the screw; a locking member which seats in the second hole of the rod holding element and has a threaded portion which extends there above; and a locking nut which engages the threaded portion of the locking member such that the rod, the screw, and the rod holding element are all securely locked together.

More particularly, with respect to the shant screw element, the elongate lower shank portion of the shaft includes the threading of a bone screw (standard or otherwise, but suited for proper purchase of the bone). The upper unthreaded portion of the screw comprises a straight shaft which is cylindrical. The lower portion of this upper shaft is tapered outward slightly. A small hexagonal bore may be disposed in the top of the upper shaft, so that a screw driving device (allen wrench, etc.) may be utilized to insert the shaft into the bone.

The rod holding element comprises a rectangular member having two holes formed therethrough. The first hole is cylindrical, having a constant diameter, for receiving the rod of the assembly therethrough. The second hole is formed transverse to the axis of the first hole, and is axially tapered. The mid portion of the two holes are partially overlapping insofar as the sidewalls of each hole are open to one another. Stated differently, when the rod is inserted into the first hole, the outer circumference of the rod is partially exposed within the volume of the second hole.

The locking member comprises a hollow cylindrical element which has an upper threaded portion and a lower tapered portion. The lower tapered portion includes a discontinuous sidewall; or, stated alternatively, the tapered portion includes at least one vertical slot formed therein. This conformation is intended to permit the lower portion of the element to expand and contract in accordance with a radial force applied to the element. The dimensions of the element are such that it may be inserted into the second hole in the rod holding element such that the tapered lower portion of the member seats against the tapered inner sidewall of the element.

As introduced above, the locking member is hollow. It includes an axial bore which is straight at the upper portion, and linearly tapered outward at the bottom designed to seat onto the upper shaft portion of the shant screw. More specifically, the locking member slides onto the upper shaft portion until the lower tapered portion of the shaft seats within the expanding and contracting lower portion of the locking member.

A simple nut is also included in the design for engaging the threaded upper portion of the locking member.

The present invention is assembled in the following manner. The locking member is first inserted into the tapered hole of the rod holding member. A retaining feature, such as a snap ring or sidewall dimple, may be included to keep the locking member within the tapered hole. The rod holding member is then slidably advanced along the rod until it is disposed in the appropriate axial location. The shant screw is then inserted into the pedicle to the desired depth, with the upper portion of the screw remaining exposed above the bone surface. The rod holding element and the locking member are then slidably advanced onto the upper portion of the shant screw until the tapered portions of the upper shaft portion and the locking member are fully nested. In this disposition, the lateral surface of the rod is in contact with the exterior of the tapered locking member via the communication between the two holes in the rod holding member.

Once so positioned, the top locking nut is advanced downwardly on the threading of the locking member until it contacts the upper portion of the rod holding element. Continued tightening action causes the locking member to be drawn upwardly relative to the rod holding element, the inner sidewalls of which apply a radially inward force onto the locking member. This causes the simultaneous exertions of force against the rod in the rod holding element and against the upper portion of the shaft screw. These exertions of force compression lock the entire assembly together in a single tightening action.

Multiple screw and coupling element assemblies are generally necessary to complete the full array of anchoring sites for the rod immobilization system, however, the pedicle screw assembly of the present invention is designed to be compatible with alternative rod systems so that, where necessary, the present invention may-be employed to rectify the failures of other systems the implantation of which may have already begun.

BRIEF DESCRIPTION OF THE FIGURES

FIG. 1 is a side view of a shant screw which is an aspect of the present invention;

FIG. 2a is a side view of a top locking nut which is an aspect of the present invention;

FIG. 2b is a side cross section view of a rod holding element which is an aspect of the present invention;

FIG. 2c is a side cross section view of a locking member which is an aspect of the present invention.

DETAILED DESCRIPTION OF THE PREFERRED EMBODIMENT

Figure 3:
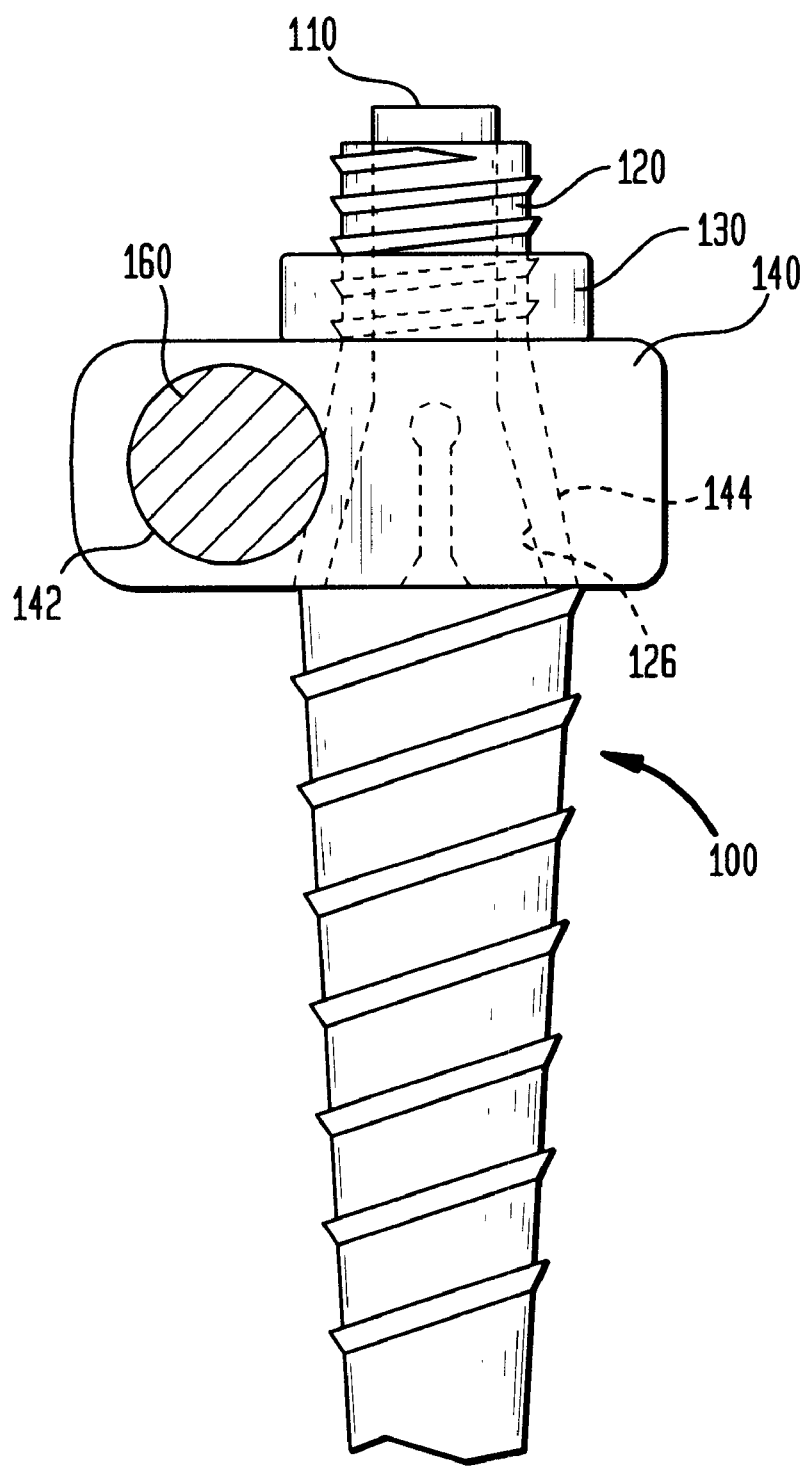
FIG. 3 is a side view of a fully assembled modular pedicle screw of the present invention.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

More particularly, referring now to FIG. 1, the shant screw 100 of the present invention comprises a lower portion 102 and an upper portion 110. The lower portion includes a bone screw threading 104. (This threading 104 may be standard or otherwise, but is in any case suited for necessary purchase of bone.) The upper portion 110 of the shant screw comprises a smooth shaft 112. This shaft 112 of the upper portion 110 may include an outwardly tapered lower portion 114, which is shown in the embodiment set forth in FIG. 1. It shall be understood that this tapering is an engineering expedient which is not critical to the functioning of the invention, but simply provides enhance gripping of the shaft 112 by the other elements of the invention.

A recess 116 may also be formed in the top of the upper portion 110 in order that the shant screw may be engaged by a suitable torque wrench and thereby be driven into the vertebral body through the pedicle.

More particularly with respect to the other elements of the invention which are associated with the upper shaft portion 110 of the shant screw 100, and referring now to FIG. 2c, another feature of the present invention is a locking member 120. This locking member 120 comprises cylindrical element, having a lower tapered portion 122 and an upper threaded portion 124. The entire locking member 120 includes an axial bore 126 which has the appropriate dimension to slide onto the upper shaft 112 of the shant screw 110. The lower tapered portion 122 is smoothly and linearly tapered outward. This lower portion 122 includes a vertical slot 128 formed in the side wall thereof, which extends sufficiently such that the lower portion 122 may expand and contract radially in accordance with a suitable pressure applied to the exterior surface of the member 120.

In the preferred embodiment, in which the upper shaft portion 112 of the shant screw 110 includes a tapered lower portion 114, the interior surface 121 of the axial bore 126 is outwardly tapered with a similar angle of taper. As previously stated, this is an engineering expedient and is not to be read as limiting of the overall scope of the invention.

The threaded upper portion 124 of the locking member is designed to receive thereon a nut 130, which is provided in a side view in FIG. 2a.

Referring now to FIG. 2b, the rod holding element 140 of the present is now described with reference to its relation to the other elements of the invention. The rod holding element 140 comprises a substantially rectangular shape having a pair of holes formed therein. The first hole 142 extends from the back to the front of the element 140 and has a constant diameter which is substantially equivalent to the diameter of the rod which is to be used in conjunction with the overall system. The second hole 144 extends from the bottom to the top of the element 140, and is tapered in approximate correspondence with the exterior taper of the locking member 120. The interior surfaces of the first and second holes intersect at the edge of each such that when the rod is inserted through the first hole 142, and the locking member 120 is inserted into the second hole 144, the exterior surfaces of each are in contact with one another.

Referring now to FIG. 3, the assembly of the present invention is now described. First the shant screw 100 is inserted into a pedicle of the patient such that the upper portion 110 of the screw extends upwardly from the posterior surface of the spine. The locking member 120 is preloaded into the tapered hole 144 of the rod holding member 140. The rod holding element 140 is then advanced along the rod 160 such that the rod slides through the first hole 142. The rod holding member 140 is then slidably advanced along the rod 160 until it is disposed in the appropriate axial location. The rod holding element 140 and the locking member 120 are then slidably advanced onto the upper portion 110 of the shant screw 100 with the upper portion 110 of the shant screw, thereby, passing through the axial bore 126. In this disposition, the lateral surface of the rod 160 within the rod holing element 140 is in contact with the exterior surface of the tapered locking member 120 via the communication between the two holes 142,144 in the rod holding member.

Once so positioned, the top locking nut 130 is advanced downwardly on the threading of the locking member 120 until it contacts the upper portion of the rod holding element 140. Continued tightening action causes the locking member 120 to be drawn upwardly relative to the rod holding element 140, the inner sidewalls of which apply a radially inward force onto the locking member 120. This causes the simultaneous exertions of force against the rod in the rod holding element and against the upper portion of the shaft screw. These exertions of force compression lock the entire assembly together in a single tightening action.

While there has been described and illustrated embodiments of a pedicle screw assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A pedicle screw assembly, comprising:
   a bone screw having a threaded lower portion and a smooth upper portion;
   a rod holding element having a first hole formed therethrough, through which a rod may be passed, and a second tapered hole formed at a transverse axis to the first hole, said first hole and second tapered hole including a shared volume defined by intersecting open side walls;
   a rod locking member which includes a cylindrical body with an axial bore which seats on the smooth upper portion of the bone screw, an upper portion of said rod locking member being threaded and said lower portion being tapered such that it may seat within the second tapered hole of said rod holding element, said lower portion of said rod locking member including at least one axial slot formed therein such that said lower portion may deflect in accordance with the application of a radial force; and
   a locking nut for engaging the threaded upper portion of the rod locking member,
   whereby tightening of the locking nut on the threading of the rod locking member causes the lower portion of the rod locking member to be compressed within the second tapered hole of the rod holding element, thus compressing against the smooth upper portion of the bone screw and compressing against the rod in the first hole of said rod holding element via said intersecting open side walls of said rod holding element.

2. The assembly as set forth in claim 1, wherein said smooth upper portion of said bone screw is tapered.

3. The assembly as set forth in claim 1, wherein said axial bore of said rod locking member is tapered.

4. The assembly as set forth in claim 2, wherein said axial bore of said rod locking member is tapered.

5. The assembly as set forth in claim 1, wherein said smooth upper portion of said bone screw includes a recess formed in a top thereof for engaging a screw driving tool.

6. The assembly as set forth in claim 1, wherein said at least one axial slot formed in the lower portion of said rod locking member comprises a single axial slot.

7. A pedicle screw and rod assembly, comprising:
   a cylindrical rod;
   at least one bone screw having a threaded lower portion and a smooth upper portion;
   a corresponding number of rod holding elements, each corresponding to one bone screw, said rod holding element having a first hole formed therethrough, through which the rod is passed, and a second tapered hole formed at a transverse axis to the first hole, said first hole and second tapered hole including a shared volume defined by intersecting open side walls;

a corresponding number of rod locking members, each corresponding to one rod locking element, which include a cylindrical body with an axial bore which seats on the smooth upper portion of the bone screw, an upper portion of said rod locking member being threaded and said lower portion being tapered such that it may seat within the second tapered hole of said rod holding element, said lower portion of said rod locking member including at least one axial slot formed therein such that said lower portion may deflect in accordance with the application of a radial force; and a corresponding number of locking nuts, each corresponding to one rod locking member, for engaging the threaded upper portion of the rod locking member, whereby tightening of the locking nut on the threading of the rod locking member causes the lower portion of the rod locking member to be compressed within the second tapered hole of the rod holding element, thus compressing against the smooth upper portion of the bone screw and compressing against the rod in the first hole of said rod holding element via said intersecting open side walls of said rod holding element.

8. The assembly as set forth in claim 7, wherein said smooth upper portion of said bone screw is tapered.

9. The assembly as set forth in claim 7, wherein said axial bore of said rod locking member is tapered.

10. The assembly as set forth in claim 8, wherein said axial bore of said rod locking member is tapered.

11. The assembly as set forth in claim 7, wherein said smooth upper portion of said bone screw includes a recess formed in a top thereof for engaging a screw driving tool.

12. The assembly as set forth in claim 7, wherein said at least one axial slot formed in the lower portion of said rod locking member comprises a single axial slot.

* * * * *